(12) United States Patent
Balkovec et al.

(10) Patent No.: US 7,691,887 B2
(45) Date of Patent: Apr. 6, 2010

(54) TRIAZOLE DERIVATIVES WHICH ARE SMO ANTAGONISTS

(75) Inventors: James M. Balkovec, Martinsville, NJ (US); Rolf Thieringer, Highland Park, NJ (US); Sherman T. Waddell, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 29 days.

(21) Appl. No.: 12/082,933

(22) Filed: Apr. 15, 2008

(65) Prior Publication Data

US 2008/0262051 A1 Oct. 23, 2008

Related U.S. Application Data

(60) Provisional application No. 60/925,018, filed on Apr. 18, 2007.

(51) Int. Cl.
- *A61K 31/41* (2006.01)
- *A01N 43/82* (2006.01)
- *A01N 43/64* (2006.01)

(52) U.S. Cl. .................. 514/364; 514/383
(58) Field of Classification Search .............. 514/364, 514/383
See application file for complete search history.

(56) References Cited

U.S. PATENT DOCUMENTS

| | | | |
|---|---|---|---|
| 6,849,636 B2 | 2/2005 | Waddell et al. | |
| 2004/0133011 A1 | 7/2004 | Waddell et al. | |
| 2006/0142245 A1 | 6/2006 | Beachy et al. | |

FOREIGN PATENT DOCUMENTS

| | | |
|---|---|---|
| WO | WO 03/065983 | 8/2003 |
| WO | WO 2004/058730 | 7/2004 |
| WO | WO 2004/106294 | 12/2004 |
| WO | WO 2005/033288 | 4/2005 |
| WO | WO 2006/017542 | 2/2006 |
| WO | WO 2006/026430 | 3/2006 |
| WO | WO 2006/028958 | 3/2006 |
| WO | WO 2006/050351 | 5/2006 |
| WO | WO 2006/050506 | 5/2006 |
| WO | WO 2006/078283 | 7/2006 |
| WO | WO 2007/047625 | 4/2007 |

OTHER PUBLICATIONS

American Cancer Society, "Can Cancer Be Prevented?" http://www.cancer.org/docroot/CRI/content/CRI_2_4_2x_Can_cancer_be_prevented.asp?sitearea=, 2009, accessed Sep. 3, 2009.*
American Cancer Society, "Can Pancreatic Cancer Be Prevented?" http://www.cancer.org/docroot/CRI/content/CRI_2_2_3X_Can_pancreatic_cancer_be_prevented_34.asp?sitearea=, 2009, accessed Sep. 3, 2009.*
American Cancer Society, "Can Prostate Cancer Be Prevented?" http://www.cancer.org/docroot/CRI/content/CRI_2_2_2X_Can_prostate_cancer_be_prevented_36.asp?sitearea=, 2009, accessed Sep. 3, 2009.*
Kinzler K and Vogelstein B, "The Genetic Basis of Human Cancer 2nd ed."Vogelstein B and Kinzler K Eds, McGraw-Hill, 2002 (p. 3 provided).*
Vippagunta SR, Brittain HG, and Grant D J, "Crystalline solids," Advanced Drug Delivery Reviews, May 2001,48(1), 3-26.*
Cooper, et al., Science, vol. 280, No. 5396, pp. 1603-1607 (1998).
Chiang, et al., Nature, vol. 383, pp. 407-413 (1996).
Bale, Nature, vol. 406, p. 944-945 (2000).
Evangelista, et al., Clinical Cancer Research, vol. 12, No. 20, pp. 5924-5928 (2006).
Kiselyov, Anti-Cancer Agents in Medicinal Chemistry, vol. 6, pp. 445-449 (2006).
Gu, et al., Bioorganic & Medicinal Chemistry Letters, vol. 15, pp. 5266-5269 (2005).
Rubin, et al., Nature, vol. 5, pp. 1026-1033 (2006).
Taipale, et al., Nature, vol. 406, pp. 1005-1009 (2000).
Bak, et al., Pharmacogenomics, vol. 4, pp. 411-429 (2003).
Keeler, et al., Teratology, vol. 1, pp. 5-10 (1968).
Incardona, et al., Development, vol. 125, pp. 3553-3562 (1998).

* cited by examiner

*Primary Examiner*—San-ming Hui
*Assistant Examiner*—Paul Zarek
(74) *Attorney, Agent, or Firm*—Matthew A. Leff; David A. Muthard

(57) ABSTRACT

The present invention provides a method for the treatment or prevention of conditions which can be ameliorated by Smo antagonism, which method comprises administration to a patient in need thereof of an effective amount of a compound of formula I or a composition comprising a compound of formula I:

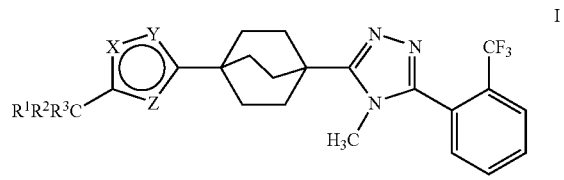

or a pharmaceutically acceptable salt or solvate thereof; wherein:
2 of X, Y and Z represent nitrogen atoms, and the other represents an oxygen atom;
$R^1$ and $R^2$ are taken together with the atom to which they are attached and represent a cyclobutyl ring, optionally substituted with 1-2 fluorine atoms, and $R^3$ represents hydrogen or a fluorine atom;
or
$R^1$ represents methyl,
$R^2$ represents methyl or a fluorine atom and
$R^3$ represents a fluorine atom.

9 Claims, No Drawings

TRIAZOLE DERIVATIVES WHICH ARE SMO ANTAGONISTS

This application claims priority from U.S. Provisional Application No. 60/925,018, filed on Apr. 18, 2007.

The present invention relates to triazole derivatives which are inhibitors of the Sonic Hedgehog pathway, in particular Smo antagonists. Thus the compounds of this invention are useful for the treatment of diseases associated with abnormal hedgehog pathway activation, including cancer, for example basal cell carcinoma, medulloblastoma, prostate, pancreatic, breast, colon, bone and small cell lung cancers, and cancers of the upper GI tract.

Hedgehog proteins (Hh) are secreted signaling proteins first discovered in *Drosophila*. They are highly hydrophobic proteins which after secretion can diffuse and establish gradients in tissues that have a paramount role in the proper development of the embryo. Three Hh homologues with different spatial and temporal distribution patterns have been identified in humans: Sonic hedgehog (SHH), Indian hedgehog (IHH) and Desert hedgehog (DHH).

The Hh signaling cascade is initiated upon binding of Hh to its receptor Patched (Ptch). In the absence of Hh, Ptch inhibits the activity of another membrane spanning protein, Smoothened (Smo) which is a key mediator of Hh signaling. Smo has a structure reminiscent of the G-protein-coupled receptor (GPCR) superfamily, but is not involved in the binding of any Hhs. When Hh is present it binds to Ptch to form an inactive complex, relieving Ptch's inhibition of Smo and activating the Hh response pathway. The Hh signal is then transmitted via a protein complex to the transcription factor cubitus interrupts (Ci) in *Drosophila* and GLI transcription factors in mammals. In the absence of Hh signaling Ci is cleaved and the amino terminal fragment acts as an inhibitor of Hh target gene transcription. Upon Hh signaling the cleavage of Ci is prevented and Ci becomes an activator of target gene transcription.

Whereas embryonic loss of SHH signaling can result in cyclopia and other developmental defects (Chiang C et al. *Nature* 383:407-413 (1996), inappropriate activation of the SHH pathway is believed to lead to increased cell proliferation and tumor formation and is associated with many different types of malignancies, including basal cell carcinoma (BCC), medulloblastoma, pancreatic cancer, small lung cancer, prostate cancer (PC), breast cancer, digestive tract tumors and skin cancer (Kiselyov A S *Anti-cancer Agents in Medicinal Chemistry* 6:445-449 (2006) and Sidransky D *Nature Genet.* 14:7-8 (1996). Thus, the Hh pathway is an important pharmacological target for a variety of conditions.

Aberrant activation of the Hh pathways in cancer are considered to be caused either by mutations in the pathway (ligand independent) or through Hh overexpression (ligand dependent).

Mutations in Ptch 1 have been connected to nevoid basal cell carcinomas syndrome (also called Gorlin syndrome), a condition characterized by a number of development defects and a predisposition for developing numerous basal cell carcinomas (BCC), medulloblastoma, rhabdomyosarcoma and several other neoplasms. Mutations which inactivate Ptch and activate Smo have also been found in sporadic BCC and medulloblastoma, and a number of other sporadic tumors (Reifenberger J et al. *Cancer Res.* 58:1798-1803 (1998) and Xie J et al. *Nature* 391:90-92 (1998).

Plant-derived teratogenic alkaloids cyclopamine and jervine have been proven to cause holoprosencephaly by direct inhibition of SHH signaling (Cooper M K et al. *Science* 280:1603-1607 (1998) and Incardona J P et al. *Development* 125:3553-3562 (1998) by binding to Smo (Chen J K et al. *Genes Dev.* 16:2743-2748 (2002). In vitro tests have shown that the teratogen cyclopamine can inhibit the abnormal cell growth of fibroblast cells from Ptch$^{-/-}$ mice, several glioblastoma/glioma cell lines, medulloblastoma cell lines, squamous cell carcinoma cell lines and SCLC cell lines (Bak M et al. *Pharmacogenomics* 4(4):411-429 (2003). Cyclopamine has also displayed efficacy in vivo in the models of medulloblastoma (Dahmane N et al. *Development* 128:5201-5212 (2001) and Berman C M et al. *Science* 297:1559-1561 (2002). Synthetic Hh antagonists have been identified in SHH responsive cell models, some targeting Smo (Chen J K et al. *Proc. Natl. Acad. Sci. USA* 99:14071-14076 (2002), Frank-Kamenetsky M et al. *J. Biol.* 1:10 (2002) and Williams J A et al. *Proc. Natl. Acad. Sci. USA* 100:4616-4621 (2003) and others an unknown target downstream of Smo (Chen J K et al. *Proc. Natl. Acad. Sci. USA* 99:14071-14076 (2002).

Reports have shown that Hh overexpression, sometimes accompanied by increased expression of Hh target genes, is detected in a broad spectrum of human tumor biopsies and cell lines, including small cell lung carcinoma, pancreatic adenocarcinoma, oesophageal, stomach and biliary tract cancers, prostate cancer, breast cancer, colon cancer and liver cancer (Rubin L L et al. *Nature Reviews Drug Discovery* 5:1026-33 (2006).

US2006/040459 describes specific triazoles as 11-beta-hydroxysteriod dehydrogenase Type 1 (11β-HSD1 or HSD1) inhibitors useful for treating metabolic disorders.

It has now surprisingly been found that these compounds are inhibitors of the Hh pathway, in particular Smo antagonists.

The present invention provides the use of a compound of structural formula I:

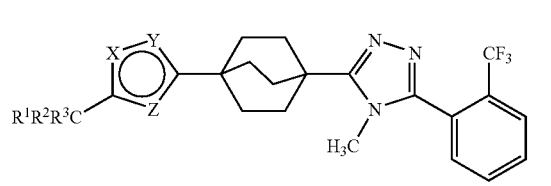

or a pharmaceutically acceptable salt or solvate thereof; wherein:

2 of X, Y and Z represent nitrogen atoms, and the other represents an oxygen atom;

$R^1$ and $R^2$ are taken together with the atom to which they are attached and represent a cyclobutyl ring, optionally substituted with 1-2 fluorine atoms, and $R^3$ represents hydrogen or a fluorine atom;

or $R^1$ represents methyl, $R^2$ represents methyl or a fluorine atom and $R^3$ represents a fluorine atom, for the manufacture of a medicament for treating or preventing conditions which can be ameliorated by Smo antagonism.

The present invention also provides a method for the treatment or prevention of conditions which can be ameliorated by Smo antagonism, which method comprises administration to a patient in need thereof of an effective amount of a compound of formula I or a composition comprising a compound of formula I.

The present invention also provides the use of a compound of formula I, or a pharmaceutically acceptable salt or solvate thereof for the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

In an embodiment one of X and Y is O and the other is N, and Z is N.

In another embodiment X is O, Y is N and Z is N.

In an embodiment $R^1$ is methyl, $R^2$ is fluorine and $R^3$ is fluorine.

In another embodiment $R^1$ and $R^2$ are taken together with the atom to which they are attached to form a cyclobutyl ring substituted by 2 fluorine atoms, and $R^3$ is hydrogen.

In another embodiment $R^1$ and $R^2$ are taken together with the atom to which they are attached to form 3,3-difluorocyclobutyl, and $R^3$ is hydrogen.

The present invention also provides the use of a compound of structural formula II:

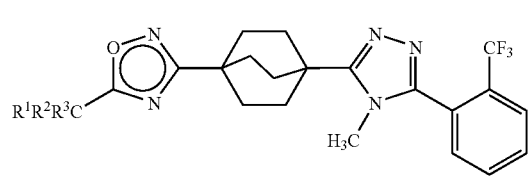

or a pharmaceutically acceptable salt or solvate thereof; wherein: $R^1$, $R^2$ and $R^3$ are as defined above, for the manufacture of a medicament for treating or preventing conditions which can be ameliorated by Smo antagonism.

The preferred identities with reference to formula II are as defined previously for formulae I mutatis mutandis.

The present invention also provides the use of the compound:
5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt or solvate thereof, for the manufacture of a medicament for treating diseases associated with Smo antagonism, such as cancer.

The present invention also provides the use of the compound:
5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt or solvate thereof, for the manufacture of a medicament for treating diseases associated with Smo antagonism, such as cancer.

The present invention also provides the use of the compound:
5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt or solvate thereof, for the manufacture of a medicament for treating diseases associated with Smo antagonism, such as cancer.

The present invention also provides the use of the compound:
2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

or a pharmaceutically acceptable salt or solvate thereof, for the manufacture of a medicament for treating diseases associated with Smo antagonism, such as cancer.

The present invention also provides the use of the compound:
2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole or a pharmaceutically acceptable salt or solvate thereof, for the manufacture of a medicament for treating diseases associated with Smo antagonism, such as cancer.

The present invention also provides the use of the compound:
2-(1-Fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

or a pharmaceutically acceptable salt or solvate thereof, for the manufacture of a medicament for treating diseases associated with Smo antagonism, such as cancer.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

The compounds may exist in a number of different polymorphic forms.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as maleic, pamoic, hydroxymaleic, glutamic, salicylic, toluenesulfonic, methanesulfonic, ethane disulfonic, oxalic, aspartic, ethanesulfonic, ethane, disulfonic, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts. In an embodiment the salt is trifluoroacetate. In another embodiment the salt is chloride.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

The present invention provides methods of inhibiting activation of the hedgehog signaling pathway, e.g., to inhibit aberrant growth states resulting from phenotypes such as Ptch loss-of-function, hedgehog gain of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

The present invention further provides methods for treating, ameliorating one or more of the symptoms of, and reducing the severity of hyperproliferative disorders, i.e. cancer, as well as other hedgehog pathway mediated disorders or conditions.

Many tumors and proliferative conditions have been shown to depend on the hedgehog pathway. The growth of such cells and survival can be affected by treatment with the compounds of the present invention. For example, small molecule inhibition of the hedgehog pathway has been shown to inhibit the growth of basal cell carcinoma (Williams et al. *PNAS* 100: 4616-21 (2003), medulloblastoma (Berman et al. *Science* 297:1559-61 (2002), pancreatic cancer, gastrointestinal cancers and esophageal cancer (Berman et al. *Nature* 425:846-51 (2003) and WO 05/013800), lung cancer (Watkins et al. *Nature* 422:313-7 (2003), and prostate cancer (Karhadkar et al. *Nature* 431: 707-12 (2004).

In addition, it has been shown that many cancer types have uncontrolled activation of the hedgehog pathway, for example, breast cancer (Kubo et al. *Cancer Research* 64:6071-4 (2004), heptacellular cancer (Patil et al. (2005) 96th Annual AACR conference, abstract #2942 and Sicklick et al. (2005) ASCO annual meeting, abstract #9610), hematological malignancies (Watkins and Matsui, unpublished results), basal carcinoma (Bale et al. *Human Molec. Genet.* B:757-762 (2001), Xie et al. *Nature* 391: 90-92 (1998), medulloblastoma (Pietsch et al. *Cancer Res.* 57: 2085-88 (1997), and gastric cancer (Ma et al. *Carcinogenesis* May 19, (2005) (EPub).

Expression of a dysfunctional mutated patched gene has been reported in sporadic and familial BCCs. Patched gene mutations or deletions have also been found in sporadic medulloblastoma, meningiomas, breast carcinoma, esophageal squamous cell carcinoma and bladder tumors (Oncogene (1998) 17, 1167-1172).

The compounds of the present invention can be used for treating or preventing conditions which can be ameliorated by Smo antagonism. The compounds of the invention are also useful for the manufacture of a medicament for treating or preventing the diseases described herein.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In an embodiment the compounds of this invention can be used for treating or preventing cancers selected from basal cell carcinoma, medulloblastoma, prostate, pancreatic, breast, colon, small cell lung cancers, sarcoma, lymphomas, leukemia, gastrointestinal cancer, multiple myeloma, glioma and heptacellular. Further cancers that can be treated or prevented by the compounds of the present invention include sporadic and familial basal cell carcinomas, sporadic medulloblastoma, meningiomas, breast carcinoma, esophageal squamous cell carcinoma and bladder cancer.

In another embodiment the compounds of this invention can be used for treating or preventing cancers selected from prostate, non-small cell lung cancers, gastrointestinal cancer and bladder cancer.

Inhibition of the hedgehog pathway has been shown to ameliorate the symptoms of psoriasis (Tas, et al., *Dermatology* 20q:126-131 (2004) and US 2004/0072913).

The present invention provides the use of a compound of formula I for the manufacture of a medicament for the treatment or prevention of psoriasis.

The present invention also provides a method for the treatment or prevention of psoriasis, which method comprises administration to a patient in need thereof of an effective amount of a compound of formula I or a composition comprising a compound of formula I Hedgehog activation has been shown to stimulate angiogenesis (Pola et al. *Nature Medicine* 7(6):706-711 (2001) and Nagase et al. *Genes to Cells* 10(6):595-604 (2005) and thus compounds which act as hedgehog antagonists may be useful as angiogenesis antagonists.

The present invention provides the use of a compound of formula I for the manufacture of a medicament for the treatment or prevention of angiogenesis.

The present invention also provides a method for the treatment or prevention of angiogenesis, which method comprises administration to a patient in need thereof of an effective amount of a compound of formula I or a composition comprising a compound of formula I Diseases caused by, supported by or associated with angiogenesis which can be treated or prevented by the compounds of formula I include cancer, ocular neovascular disease, age-related macular degeneration, diabetic retinopathy, retinopathy of prematurity, corneal graft rejection, neovascular glaucoma, retrolental fibroplasia, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Stevens Johnson disease, periphigoid radial keratotomy, corneal graph rejection, rheumatoid 15 arthritis, osteoarthritis chronic inflammation (e.g., ulcerative colitis or Crohn's disease), hemangioma, Osler-Weber-Rendu disease, and hereditary hemorrhagic telangiectasia.

In an embodiment the compounds of the present invention are useful for treating and preventing cancers associated with patched loss-of function.

In another embodiment the compounds of the present invention are useful for treating and preventing cancers associated with smoothened gain-of function.

The compounds of formula I are also useful as chemo- and radiosensitizers for cancer treatment. They are useful for the treatment of mammals who have previously undergone or are presently undergoing or will be undergoing treatment for cancer. Such other treatments include chemotherapy, radiation therapy, surgery or immunotherapy, such as cancer vaccines.

The instant compounds are particularly useful in combination with therapeutic, anti-cancer and/or radiotherapeutic agents. Thus, the present invention provides a combination of the presently compounds of formula I with therapeutic, anti-cancer and/or radiotherapeutic agents for simultaneous, separate or sequential administration. The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent, anti-cancer agent and/or radiation therapy can be administered according to therapeutic protocols well known in the art. It will be apparent to those skilled in the art that the administration of the therapeutic agent, anti-cancer agent and/or radiation therapy can be varied depending on the disease being treated and the known effects of the anti-cancer agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse affects.

In one embodiment, the compounds of formula I can be administered in combination with one or more agent selected from an anti-inflammatory agent, antihistamine, anti-cancer agent, immunomodulator, therapeutic antibody and a protein kinase inhibitor, e.g., a tyrosine kinase inhibitor.

In another embodiment is provided a combination of a compound of formula I and an anti-cancer agent for simultaneous, separate or sequential administration.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers and WO 2006/061638. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. Examples of such agents are provided in WO 2006/061638.

Anticancer agents suitable for use in the combination therapy of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-161, and Teniposide [VM-261, etc.), and agents that target topoisomerase I (e.g., Camptothecin and Isirinotecan [CPT-111, etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adrianycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., alltransretinoic acid, etc.); 13) gene therapy techniques; 14) antisense therapy techniques; 15) tumor vaccines; 16) therapies directed against tumor metastases (e.g., Batimistat, etc.); 17) inhibitors of angiogenesis and kinase inhibitors.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Suitable therapeutic antibodies for use in the combination therapy of the present invention include antibodies directed against the HER2 protein, such as trastuzuinab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like.

In an embodiment is provided a method of treating or preventing basal cell carcinoma, pancreatic cancer, prostate cancer, sarcoma, lymphomas, leukemia, gastrointestinal cancer, multiple myeloma, small cell lung cancer, glioma, breast cancer, heptacellular, or medulloblastoma, which method comprises administration to a patient in need thereof of an effective amount of a compound of formula I in combination with another anti-cancer agent.

In an embodiment is provided a method of treating or preventing psoriasis, which method comprises administration to a patient in need thereof of an effective amount of a compound of formula I in combination with one or more other anti-psoriasis agents including, but not limited to, corticosteroids, tar, calcipotriene, tazarotene, calcineurin inhibitors, ultraviolet irradiation, methotrexate, retinoids, cyclosporine, immunomodulatory drugs, etanercept, alefacept, efalizumab, and infliximab.

The compounds of the formula can be used in combination with radiation therapy. The phrase "radiation therapy" refers to the use of electromagnetic or particulate radiation in the treatment of neoplasia and includes the use of ionizing and non-ionizing radiation.

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be useful for treating or preventing cancer in combination with siRNA therapeutics.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyr®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANCLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Inplant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Where the synthesis of intermediates and starting materials is not described, these compounds are commercially available or can be made from commercially available compounds by standard methods or by extension of the synthesis above, schemes and Examples herein.

Compounds of formula I may be converted to other compounds of formula I by known methods or by methods described in the Examples herein.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc (tert-butoxycarbonyl) or benzylcarbonyl protecting group is present, it may be removed by the addition of solvents such as TFA, DCM and/or MeCN at about room temperature. The compound may also be hydrogenated using standard methods, such as treating with a catalyst such as Pd/C, in a solvent such as methanol under a hydrogen atmosphere. EtOAc in the presence of HCl and 1,4-dioxane may also be added to remove the Boc or benzylcarbonyl protecting group, at about room temperature.

When the compounds of the present invention have chiral centres, the enantiomers may be separated from the racemic mixtures by standard separating methods such as using SFC.

The exemplified compounds described herein and tested by the assays described below were found to have an $IC_{50}$ value of less than 25 uM.

Abbreviations Used in the Description

AIBN: 2,2'-azobisisobutyronitrile; BOC: t-butyloxycarbonyl; 9-BBN: 9-borabicyclo[3.3.1]nonane; Bn: Benzyl; nBuLi: n-butyl lithium; Cbz: benzyloxycarbonyl; CDI: 1,1'-carbonyldiimidazole; MeOTf: methyl trifluoromethanesulfonate; $(COCl)_2$: oxalyl chloride; DAST: (diethylamino) sulfur trifluoride; DCM: dichloromethane; DIEA: diisopropylethylamine; DMAP: 4-(dimethylamino)pyridine; DMC: 2-chloro-1,3-dimethylimidazolinium chloride; DMF: N,N-dimethylformamide; Et: Ethyl; $Et_3N$: Triethylamine; EtOAc: ethyl acetate; EtOH: Ethanol; $Et_2Zn$: Diethylzinc; FCS: fetal bovine serum; HATU: O-(7-azabenzotriazol)-N, N,N',N'-tetramethyluronium haxafluorophosphate; Me: Methyl; MeCN: Acetonitrile; MeOH: Methanol; mCPBA: meta-chloroperbenzoic acid; MS: mass spectrum; NaOAc: sodium acetate; NBS: N-bromosuccinimide; PBS: Phosphate buffered saline; Ph: Phenyl; PyBROP: bromotripyrrolidino-phosphonium hexafluorophosphate; $PPh_3$: triphenylphosphine; pyr: Pyridine; $SOCl_2$: thionyl chloride; TFA: trifluoroacetic acid; TFFH: N,N,N',N'-tetramethylformamidinium hexafluorophosphate; THF: tetrahydrofuran; TLC: thin-layer chromatography; and TsOH: p-toluenesulfonic acid;

Shh-Light II Reporter Assay

Assay designed to measure firefly and Renilla luciferase, in the same well.

Prior to assay the Shh-Light II cells (ATCC Catalog No. CRL-2795) were cultured in growth media Assay Protocol:

Day −1: seed 60,000 Shh-Light II cells in assay medium 75 uL/well, in presence of DMSO/inhibitor.

Day 0: after overnight incubation at 37° C. 10% $CO_2$ add 3 uM of Purmorphamine (Calbiochem 540220) in water.

Day 1: After 30 hrs at 37° C. 10% $CO_2$ of incubation develop the assay, directly to cells in growth medium.

Add 75 µl of DualGlow Luciferase Reagent (Promega, E2940)
Incubate 10 min. in the dark
Read plate at Luminometer: TopCount, by PerkinElmer
Add 75 ul of DualGlow Stop & Glow
Incubate 10 min. in the dark
Read plate at Luminometer: TopCount, by PerkinElmer
Output is the ratio between FireFly/Renilla counts Growth Media:

For Growth:

DMEM: Dulbecco's Mod Eagle Medium with 0.11 G/L Pyr, with Pyridoxine. (GIBCO Cat No: 41966-029). The medium has complemented with 10% FCS (fetal bovine serum), 1% Penicillin-Streptomycin (10 mg/ml) (GIBCO, 15140-114) and 1% L-Glutamine 200 mM (100×) (GIBCO, 3042190) and 0.4 mg/ml of G418 (Roche) and 0.15 mg/ml Zeocyne (Invitrogen R-250-01). Cells cultured at 10% $CO_2$.

For Assay:

DMEM: Dulbecco's Mod Eagle Medium with 0.11 G/L Pyr, with Pyridoxine. (GIBCO Cat No: 21063-045), without Phenol Red. The medium has complemented with 2% FCS (fetal bovine serum), 1% Penicillin-Streptomycin (10 mg/ml) (GIBCO, 15140-114) and 1% L-Glutamine 200mM (100×) (GIBCO, 3042190). Cells cultured at 10% $CO_2$. DMSO 0.25%.

SHH Smo Binding Assay

In transfected Cos7 cells we are able to measure the binding of SMO ligand Cyclopamine-bodipy.

Assay Protocol:

Day −1: Seed 3,500,000 Cos7 cells in Petri dish 10 cm.

Day 0: Transfect cells with Lipofectamine2000 (Invitrogen) and plasmid pSMO-Myc. After 5 hrs seed the cells in 96 well plate in growth DMEM (10% FCS); 15,000 cells per 100 ul well.

Day 1: 24 hrs after transfection, change the medium with assay DMEM (without Phenol Red 2% FCS) and add compound/DMSO 0.5%. Incubate at 37° C. 5% CO2.

Day 2: After 16 hrs, add Cyclopamine-Bodipy (Toronto Research Chemical, B674800) at the final concentration of 50 nM. Incubate for 4 hrs at 37° C. 5% $CO_2$. Then cells are fixed 10 minutes with 3.5% Formaldehyde 100 ul/well. Cells are washed 3 times with PBS and nuclei are stained with 1.5 uM Propidium Iodide. Read at Acumen Explorer.

Growth Media:

For Growth:

DMEM: GIBCO Dulbecco's Mod Eagle Medium with 0.11 G/L Pyr, with Pyridoxine (GIBCO, 41966-029). The medium has complemented with 10% FCS (GIBCO, 10106-169), 1% Penicillin-Streptomycin (10 mg/ml) (GIBCO, 15140-114) and 1% L-Glutamine 200 mM (100×) (GIBCO, 3042190). Cells cultured at 5% $CO_2$ For Assay:

DMEM: GIBCO Dulbecco's Mod Eagle Medium with 0.11 G/L Pyr, with Pyridoxine (GIBCO, 21063-045) without Phenol Red. The medium has complemented with 2% FCS (GIBCO, 10106-169), 1% Penicillin-Streptomycin (10 mg/ml) (GIBCO, 15140-114) and 1% L-Glutamine 200 mM (100×) (GIBCO, 3042190). Cells cultured at 5% $CO_2$. DMSO 0.5%.

Anti-Proliferative Activity on Murine Medulloblastoma Cells

The ability of Smo antagonists to inhibit the proliferation of using primary, allograft-expanded murine medulloblastoma cells was measured. In contrast to established tumor cell lines, the HH pathway is kept active in these cells after explanation, and tumors maintain a specific dependency on HH pathway activation for their survival/proliferation. The concentration required to inhibit cell growth by 50% ($CC_{50}$) was determined in the absence or presence of a synthetic Smo agonist.

Medulloblastoma cells were obtained from explanted tumors (Oncogene (2002) 21, 7580-7584) and resuspended in NPMM at a concentration of 100,000 cells/mL and seeded into a 96-well microplate at an initial concentration of 5000 cells/well in 100 uL of NPMM. Smo antagonists were added with serial dilutions over 7 points (0.03-25 uM concentration range, 0.25% DMSO), in the absence or presence of 0.3 uM of the synthetic agonist. The cells were then incubated for 96 h at 37° C. under 5% $CO_2$, and for additional 24 h after the addition of BrdU. Cells were then fixed and processed for the detection of DNA-incorporated BrdU using the BrdU Chemiluminescent Immunossay Kit (Roche Applied Science Cat. No. 11669915001), following the manufacturer's instructions. Signal was measured using a Top Count instrument (Perkin Elmer) and $CC_{50}$ values were determined based on the residual BrdU incorporation in the presence of increasing concentrations of antagonist.

A compound from this invention was able to inhibit medulloblastoma cell proliferation in a dose-dependent manner. This block was overcome by the addition of a selective Smo agonist, suggesting that proliferation inhibition was selectively due to interference with HH signaling in these cells. The $CC_{50}$ measured in the absence of the agonist was 0.3 uM while the addition of agonist shifted the $CC_{50}$ to greater than 30 uM. Similar activity can reasonably be expected for all other structurally related compounds within the narrow scope of the present invention.

Effect of Smo Antagonist on the Growth of Subcutaneously Implanted, Primary Mouse Medulloblastomas Xenografts The ability of a compound from this invention to inhibit the growth of a hedgehog signaling-dependent tumor in vivo was assessed. A xenograft model was used with primary medulloblastomas derived from Ptch-1 heterozygous mice that were irradiated after birth.

Medulloblastoma tumors, derived from cerebella of postnatally irradiated Ptch −/+ mice (Oncogene (2002) 21, 7580-7584), were serially passaged in vivo subcutaneously. For this study tumors were explanted and single cell suspensions of medulloblastoma cells were injected subcutaneously (2.5 millions cells/mouse) in the presence of 50% Matrigel in 5-weeks old immune compromised mice. When tumors reached an average volume of 150 mm mice were randomized and treated per os with 40 mg/kg or 80 mg/kg qd, or 80 mg/kg bid with a compound from this invention diluted in 0.5% methylcellulose. Control mice were treated with the same volumes of vehicle only. Tumor volumes were measured twice a week.

This experiment demonstrated that a compound from this invention elicited tumor growth inhibition at doses of 40 and 80 mg/kg/day and led to tumor shrinkage at a dose of 80 mg/kg bid.

Similar activity can reasonably be expected for all other structurally related compounds within the narrow scope of the present invention.

EXAMPLE 1

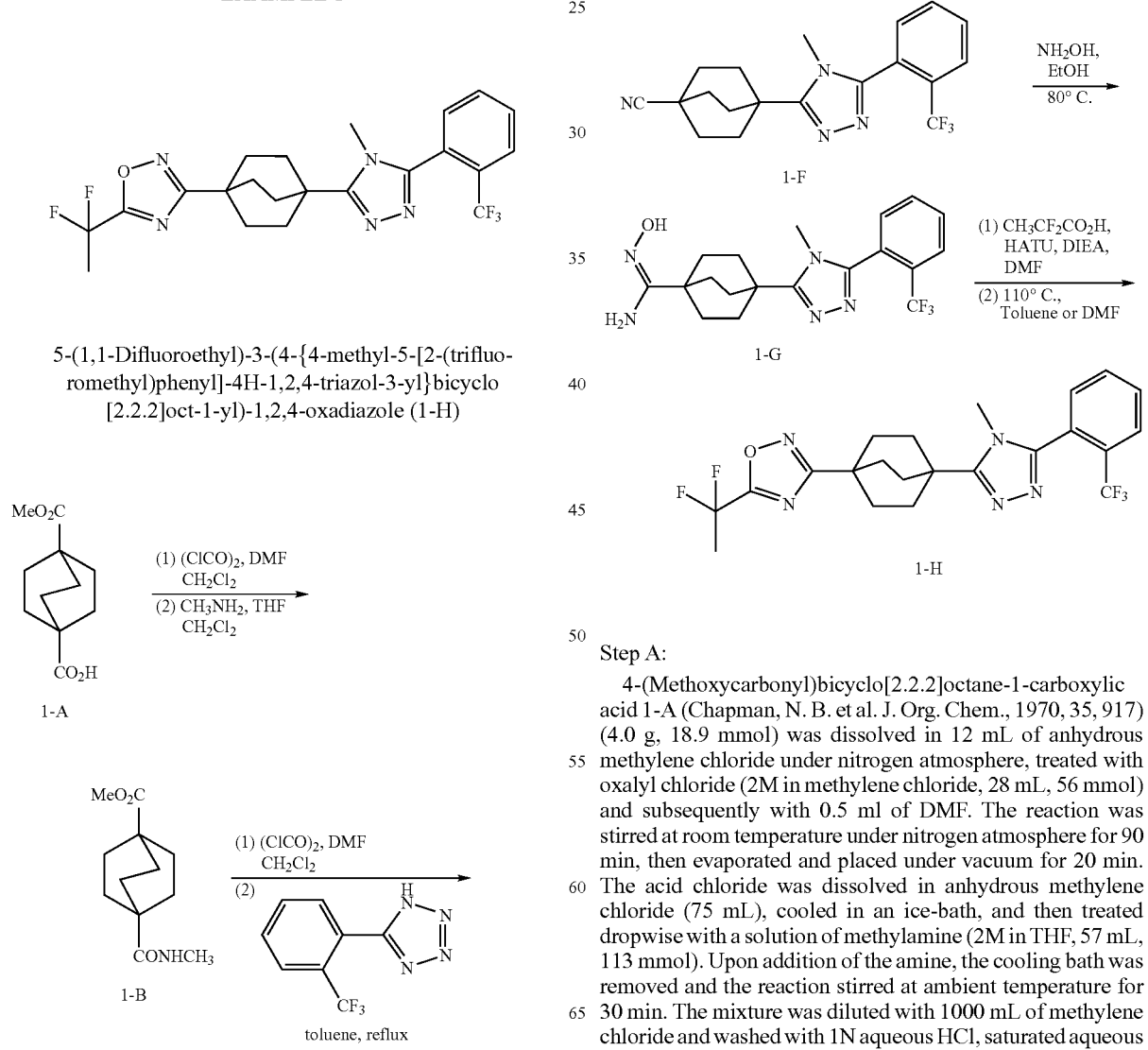

5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (1-H)

Step A:

4-(Methoxycarbonyl)bicyclo[2.2.2]octane-1-carboxylic acid 1-A (Chapman, N. B. et al. J. Org. Chem., 1970, 35, 917) (4.0 g, 18.9 mmol) was dissolved in 12 mL of anhydrous methylene chloride under nitrogen atmosphere, treated with oxalyl chloride (2M in methylene chloride, 28 mL, 56 mmol) and subsequently with 0.5 ml of DMF. The reaction was stirred at room temperature under nitrogen atmosphere for 90 min, then evaporated and placed under vacuum for 20 min. The acid chloride was dissolved in anhydrous methylene chloride (75 mL), cooled in an ice-bath, and then treated dropwise with a solution of methylamine (2M in THF, 57 mL, 113 mmol). Upon addition of the amine, the cooling bath was removed and the reaction stirred at ambient temperature for 30 min. The mixture was diluted with 1000 mL of methylene chloride and washed with 1N aqueous HCl, saturated aqueous sodium bicarbonate, and brine. The organic layer was dried over anhydrous sodium sulfate and evaporated. Product was purified by flash silica gel chromatography, eluting with 0-5% MeOH/CH$_2$Cl$_2$ gradient to yield methyl 4-[(methylamino)carbonyl]bicyclo[2.2.2]octane-1-carboxylate 1-B as a white solid. MS (ESI$^+$)=226.2 (M+1).

Step B:

Methyl 4-[(methylamino)carbonyl]bicyclo[2.2.2]octane-1-carboxylate 1-B (2.76 g, 12.3 mmol) was dissolved in methylene chloride (100 ml), and oxalyl chloride (2.0 M in DCM, 15.3 ml) was added to the resulting solution followed by DMF (0.19 ml, 2.45 mmol). The reaction mixture was then stirred at room temperature under nitrogen for 2 hours before it was concentrated and stripped with toluene 3 times. The residue was redissolved in toluene (100 ml), treated with 5-[2-(trifluoromethyl)phenyl]-1H-tetrazole (3.15 g, 14.7 mmol) and refluxed under nitrogen for 12 hours. The product, 1,2,4-triazole 1-C, which precipitated out of reaction mixture as the HCl salt, was dissolved in DCM, washed twice with saturated aqueous sodium bicarbonate solution, dried (MgSO$_4$) and stripped to yield a white solid. MS (ESI$^+$)=394.2 (M+1); $^1$H NMR (500 MHz, CDCl$_3$): δ 2.00 (6H, m), 2.18 (6H, m), 3.48 (3H, s), 3.72 (3H, s), 7.51 (1H, m), 7.71 (2H, m), 7.85 (1H, m) ppm.

Step C:

A solution of methyl ester 1-C (1.19 g, 3.0 mmol) in 5% H$_2$O/MeOH (30 ml) was treated with KOH (0.51 g, 9.0 mmol) at 60° C. under nitrogen atmosphere for 18 h. The resulting mixture was concentrated, diluted with water (150 ml), washed with EtOAc and acidified with aqueous HCl (1 N) to pH=3. The precipitate was filtered, washed with a small amount of water and ether and dried under vacuum to yield a pink solid (4-{4-methyl-5-[2-(trifluoromethyl)phenyl]-4H-1,2,4-triazol-3-yl}bicyclo[2.2.2]octane-1-carboxylic acid (1-D). $^1$H NMR (500 MHz, CD$_3$OD): δ 2.00 (6H, m), 2.17 (6H, m), 3.55 (3H, s), 7.62 (1H, m), 7.85 (2H, m), 7.96 (1H, m) ppm.

Step D:

A portion of solid 4-{4-methyl-5-[2-(trifluoromethyl)phenyl]-4H-1,2,4-triazol-3-yl}bicyclo[2.2.2]octane-1-carboxylic acid (1-D, 0.67 g, 1.77 mmol) was suspended in CH$_2$Cl$_2$ (15 ml) and treated with 1',1'-carbonyldiimidazole (0.57 g, 3.54 mmol) at room temperature under nitrogen atmosphere. After 2 h, concentrated ammonium hydroxide was added (40 ml) and the reaction was stirred for 18 h. The crude mixture was diluted with water (150 ml) and extracted with 3 portions of CH$_2$Cl$_2$ (70 ml). The organic washes were combined, washed with brine, dried over Na$_2$SO$_4$, and the solvent was removed under reduced pressure to yield carboxamide 1-E as a white powder. MS (ESI$^+$)=379.3 (M+1).

Step E:

A solution of carboxamide 1-E (0.64 g, 1.7 mmol) and cyanuric chloride (0.47 g, 2.53 mmol) in DMF (15 ml) was stirred at room temperature under nitrogen atmosphere. After 2 h, DMF was removed in vacuo and the solid was redissolved in CH$_2$Cl$_2$ (100 ml) and washed with saturated aqueous sodium bicarbonate and brine, dried (Na$_2$SO$_4$), and the solvent was removed under reduced pressure to give the nitrile 1-F as a pale yellow solid. MS (ESI$^+$)=361.3 (M+1); $^1$H NMR (500 MHz, CDCl$_3$): δ 2.15 (6H, m), 2.22 (6H, m), 3.47 (3H, s), 7.51 (1H, m), 7.72 (2H, m), 7.87 (1H, m) ppm.

Step F:

A solution of nitrile 1-F (0.56 g, 1.6 mmol) and hydroxylamine (50% aqueous, 4 ml) in ethanol (40 ml) was heated at 80° C. for 18 h. The resulting mixture was cooled to room temperature and concentrated in vacuo. The solid was suspended in toluene, the solvent removed in vacuo, and the solid (1-G) was dried under reduced pressure, and used in the next step without further purification. MS (ESI$^+$)=394.3 (M+1).

Step G:

HATU ((2.93 g, 7.63 mmol) was added to a solution of 2,2-difluoropropinic acid (0.84 g, 7.63 mmol) and N'-hydroxy-4-{4-methyl-5-[2-(trifluoromethyl)phenyl]-4H-1,2,4-triazol-3-yl}bicyclo[2.2.2]octane-1-carboximidamide (1-G) (1.0 g, 2.54 mmol) in anhydrous DMF (30 ml), followed by DIEA (2.2 ml, 12.7 mmol). The resulting mixture was stirred at room temperature for 48 hours, then heated to 110° C. for 3 hours. After cooling to room temperature, the solvent was removed under reduced pressure. The residue was dissolved in ethyl acetate, washed with water, saturated sodium bicarbonate and brine. The crude product was purified by column chromatography with 100% ethyl acetate as eluent to give 1-H as a white powder. MS (ESI$^+$)=468.3 (M+1); $^1$H NMR (500 MHz, CDCl$_3$): δ 2.10-2.34 (15H, m), 3.57 (3H, s), 7.73-7.75 (3H, m), 7.86 (1H, m) ppm. Shh-Light II Assay: IC$_{50}$: 35% inhibition at 5 μM.

EXAMPLE 2

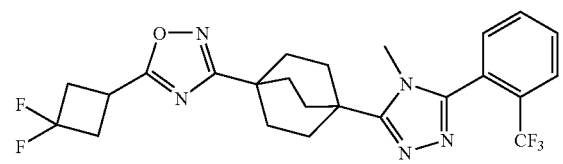

5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole (2-E)

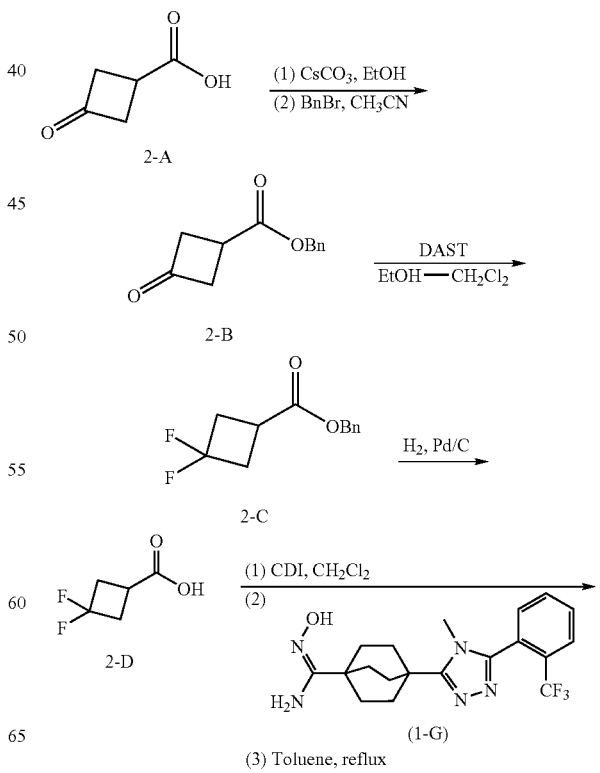

-continued

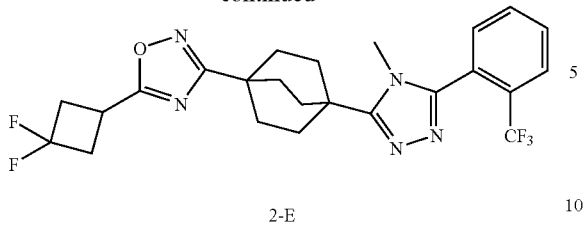

2-E

Step A:

3-Oxocyclobutanecarboxylic acid (2-A) (1.0 g, 10.0 mmol) was dissolved in anhydrous ethanol (25 ml), and cesium carbonate (1.66 g, 5.1 mmol) was added. After stirring at room temperature under nitrogen for 4 hours, the reaction mixture was concentrated. The residue was redissolved in anhydrous acetonitrile (50 ml) and treated with benzyl bromide (1.2 ml, 10.0 ml). The mixture was allowed to stir at room temperature under nitrogen for 12 hours. Solvent was then removed under reduced pressure and the residue was partitioned between ethyl acetate and water. The crude product was purified with silica gel chromatography eluting with a gradient of 100% hexane to 96% hexane/ethyl acetate to give 2-B. $^1$H NMR (500 MHz, CDCl$_3$): δ 3.30-3.48 (5H, m), 5.22 (2H, s), 7.37-7.41 (5H, m) ppm.

Step B:

Benzyl 3-oxocyclobutanecarboxylate (2-B) (1.23 g, 6.03 mmol) was dissolved in methylene chloride (35 ml). DAST (8.0 ml, 6.03 mmol) was added under nitrogen, followed by anhydrous ethanol (0.4 ml, 7.23 mmol). The mixture was stirred for 12 hours before it was diluted with methylene chloride, washed successively with saturated sodium bicarbonate, 1N aq. hydrochloric acid, and brine. The organic layer was dried over anhydrous sodium sulfate, filtered and concentrated. The crude product was purified by silica gel chromatography with 93% hexane/ethyl acetate as eluent to give 2-C as an oil. $^1$H NMR (500 MHz, CDCl$_3$): δ 2.81-2.93 (4H, m), 3.01-3.04 (1H, m), 5.20 (2H, s), 7.36-7.42 (5H, m) ppm.

Step C:

Benzyl 3,3-difluorocyclobutanecarboxylate (2-C) (0.84 g, 3.72 mmol) was dissolved in ethanol (40 ml), and approximately 20 mg of palladium on activated carbon was added. The mixture was stirred at room temperature under hydrogen atmosphere for 12 hours, and then filtered through a pad of Celite. The filtrates were concentrated and dried in vacuo to give 2-D. $^1$H NMR (500 MHz, CDCl$_3$): δ 2.86-2.93 (4H, m), 3.02-3.04 (1H, m) ppm.

Step D:

N'-Hydroxy-4-{4-methyl-5-[2-(trifluoromethyl)phenyl]-4H-1,2,4-triazol-3-yl}bicyclo[2.2.2]octane-1-carboximidamide (1-G) (120 mg, 0.305 mmol) was added to a pre-stirred solution of 3,3-difluorocyclobutanecarboxylic acid 2-D (166 mg, 1.22 mmol) and carbonyldiimidazole (198 mg, 1.22 mmol) in CH$_2$Cl$_2$ (8 ml). The resulting mixture was stirred at room temperature for 48 h, then concentrated. The solid was resuspended in toluene and refluxed under nitrogen atmosphere for 3 h. The product was purified by C-18 reverse phase HPLC eluting with 30-80% acetonitrile/water with 0.1% TFA to yield 2-E as a white powder. MS (ESI$^+$)=494.2 (M+1); $^1$H NMR (500 MHz, CDCl$_3$): δ 2.09 (6H, m), 2.31 (6H, m), 3.03-3.11 (4H, m), 3.57-3.61 (4H, m), 7.56 (1H, m), 7.71 (2H, m), 7.86 (1H, m) ppm. Shh-Light II Assay: IC$_{50}$: 1.4 μM.

EXAMPLE 3

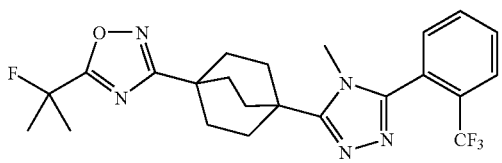

5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (3-A)

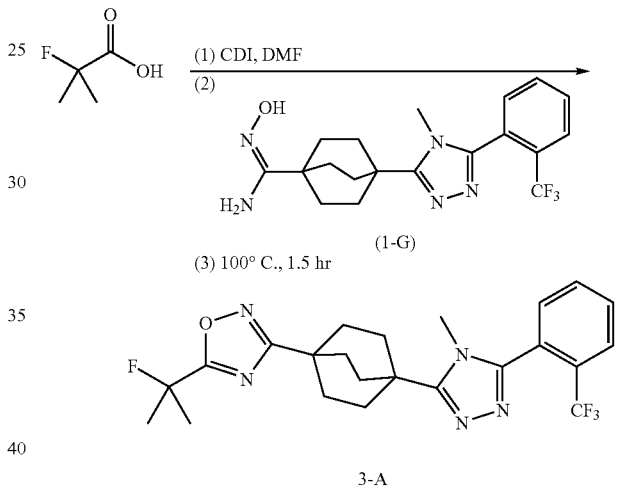

A solution of 2-methyl-2-fluoropropionic acid (108 mg, 1.02 mmol) and 1'1'-carbonyldiimidazole (144 mg, 0.888 mmol) in anhydrous DMF (2.5 ml) was stirred at room temperature under nitrogen atmosphere for 30 min. To this was added N'-Hydroxy-4-{4-methyl-5-[2-(trifluoromethyl)phenyl]-4H-1,2,4-triazol-3-yl}bicyclo[2.2.2]octane-1-carboximidamide (1-G) (139.5 mg, 0.355 mmol) and the solution stirred overnight under N$_2$. The reaction was heated for 1.5 hr at 100° C. in a heat block. DMF was removed in vacuo and the solid was redissolved in CH$_3$CN (4 ml). The product was purified by C-18 reverse phase chromatography eluting with 10-90% CH$_3$CN (0.1% TFA)/water (0.1% TFA). The solvent was removed and the residue taken up in DCM and free-based from saturated aqueous sodium bicarbonate solution. The organic layers were dried over MgSO$_4$ and filtered. The solvent was replaced with CH$_3$CN/water and lyophilized to afford 5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole (3-A) as a white solid. MS (ESI$^+$)=464.13 (M+1). $^1$H NMR (500 MHz, CDCl$_3$): δ 7.89-7.85 (m, 1H), 7.75-7.69 (m, 2H), 7.55 (t, 1H), 3.52 (s, 3H), 2.30 (dd, 6H), 2.15 (dd, 6H), 1.90 (s, 3H), 1.86 (s, 3H). Shh-Light II Assay: IC$_{50}$: 4.2 μM.

EXAMPLE 4

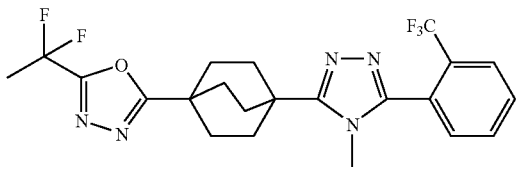

2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (4-B)

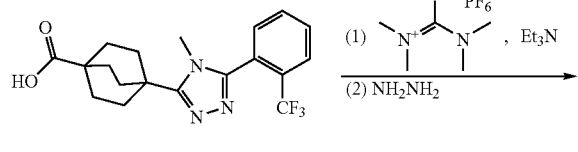

1-D

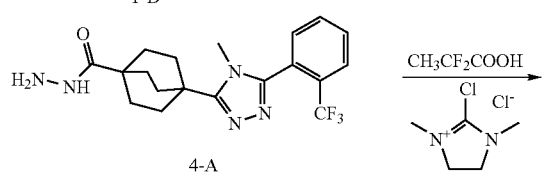

4-A

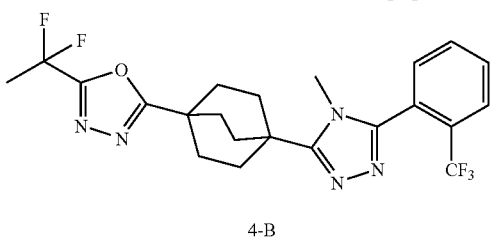

4-B

Step A:

Acid 1-D (1.0 g, 2.64 mmol) was dissolved in DMF (30 ml), and TFFH (0.84 g, 3.18 mmol) was added followed by triethylamine (0.88 ml, 6.34 mmol) and anhydrous hydrazine (0.12 ml, 3.95 mmol). The mixture was stirred at room temperature under nitrogen for 12 hours. The mixture was then concentrated under reduced pressure to remove DMF. The residue was taken up in ethyl acetate and washed with saturated sodium bicarbonate and brine. The organic layer was dried over anhydrous sodium sulfate, filtered and concentrated. The product (4-{4-methyl-5-[2-(trifluoromethyl)phenyl]-4H-1,2,4-triazol-3-yl}bicyclo[2.2.2]octane-1-carbohydrazide, 4-A) was further dried by co-evaporating with toluene several times before being used in the next step.

MS (ESI$^+$)=394.2 (M+1).

Step B:

A mixture of 4-{4-methyl-5-[2-(trifluoromethyl)phenyl]-4H-1,2,4-triazol-3-yl}bicyclo[2.2.2]octane-1-carbohydrazide (4-A) (334 mg, 0.850 mmol) and 2,2-difluoropropionic acid (78 mg, 0.708 mmol) was suspended in methylene chloride, and DMC (1.2 g, 7.08 mmol) was added as solid. The mixture was stirred at room temperature under nitrogen for 48 hours before it was diluted with methylene chloride, washed with water, saturated sodium bicarbonate and brine. The crude product was purified by column chromatography to give 4-B as a white solid. MS (ESI$^+$)=468.3 (M+1); $^1$H NMR (500 MHz, CDCl$_3$): δ 2.15-2.33 (15H, m), 3.52 (3H, s), 7.61 (1H, m), 7.72 (2H, m), 7.85 (1H, m) ppm. Shh-Light II Assay: IC$_{50}$: 9.3 μM.

EXAMPLE 5

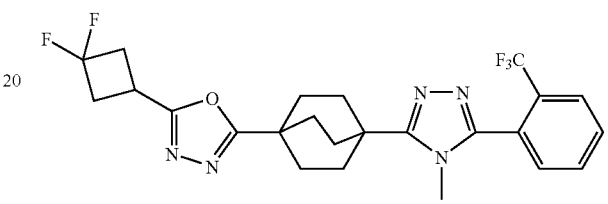

2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole (5-A)

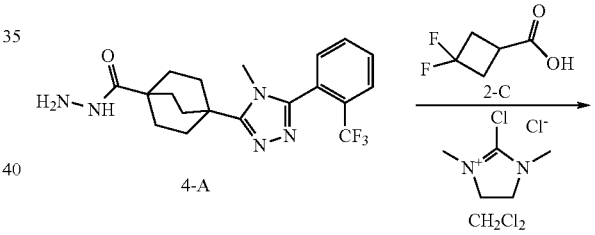

4-A

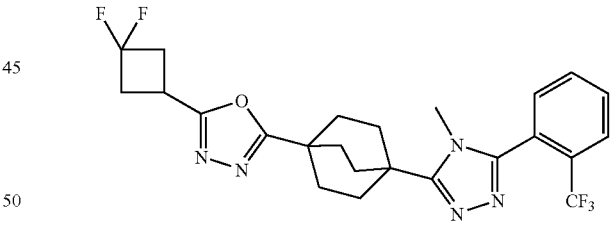

5-A

Step A:

Triazole 5-A was prepared from hydrazide 4-A (119 mg, 0.303 mmol) and 3,3-difluorocyclobutanecarboxylic acid (49.4 mg, 0.363 mmol) using the method described in Example 4, step B. 2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole (5-A) was isolated as a white powder after purification by C-18 reverse phase HPLC two times (eluting with 20-80% and 25-50% acetonitrile/water, respectively, with 0.1% TFA). MS (ESI$^+$)= 494.2 (M+1). Shh-Light II Assay: IC$_{50}$: 2 μM.

EXAMPLE 6

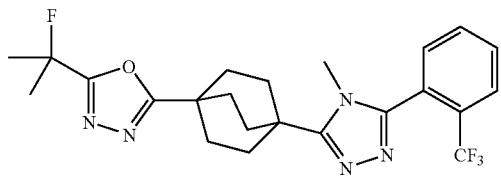

2-(1-Fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (6-B)

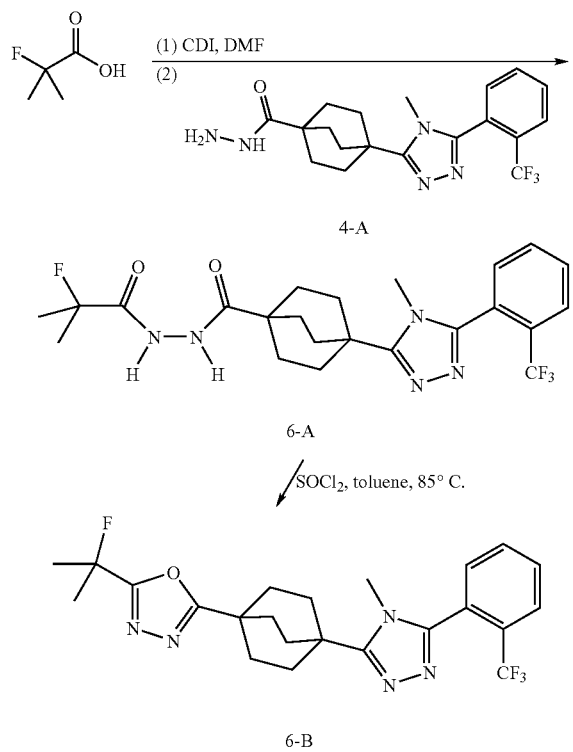

Step A:

A solution of 2-methyl-2-fluoropropionic acid (70 mg, 0.66 mmol) and 1'1'-carbonyldiimidazole (107 mg, 0.66 mmol) in anhydrous DMF (2 ml) was stirred at room temperature under nitrogen atmosphere for 30 min. To this solution was added hydrazide 4-A (200 mg, 0.509 mmol) and the solution was stirred overnight under $N_2$. DMF was removed in vacuo and the solid was redissolved in $CH_3CN$ (4 ml) with some DMSO. Product was purified by C-18 reverse phase chromatography eluting with 10-90% $CH_3CN$ (0.1% TFA)/water (0.1% TFA). Solvent was removed in vacuo and the product was free-based from DCM and saturated aqueous sodium bicarbonate. The organic layer was dried over $MgSO_4$ and filtered. The solvent was removed to afford product 6-A. MS (ESI$^+$)=482.30 (M+1).

Step B:

To the material obtained in Step A was added toluene (3 mL) and thionyl chloride (2 mL) and, fitted with a reflux condenser, the solution was heated to 85° C. under nitrogen. After 1 hour the solvent was removed under reduced pressure and the residue was dissolved in toluene which was removed under reduced pressure. The residue was dissolved in $CH_3CN$ (4 ml) and the product was purified by C-18 reverse phase chromatography eluting with 10-90% $CH_3CN$ (0.1% TFA)/water (0.1% TFA). Solvent was removed in vacuo and the product was free-based from DCM and saturated aqueous sodium bicarbonate. The organic layer was washed with brine and dried over $MgSO_4$ and filtered. The solvent was removed and the product lyopholyzed from $CH_3CN$ and water to afford 2-(1-fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole (6-B) as a white solid. MS (ESI$^+$)=463.98 (M+); $^1$H NMR (500 MHz, CDCl$_3$): δ 7.89-7.85 (m, 1H), 7.76-7.70 (m, 2H), 7.58 (s, 1H), 3.53 (s, 3H), 2.32 (dd, 6H), 2.20 (dd, 6H), 1.92 (s, 3H), 1.87 (s, 3H).

The invention claimed is:

1. A method for the treatment of a Hedgehog-expressing cancer selected from the group consisting of basal cell carcinoma, prostate cancer, pancreatic cancer, small cell lung cancer, gastrointestinal cancer, and medulloblastoma, which method comprises administration to a patient in need thereof of an effective amount of a compound of formula I or a composition comprising a compound of formula I:

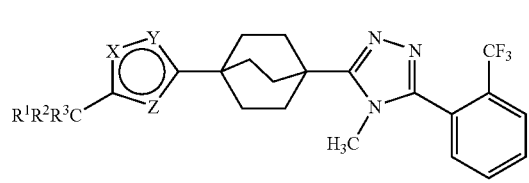

or a pharmaceutically acceptable salt thereof; wherein:
   2 of X, Y and Z represent nitrogen atoms, and the other represents an oxygen atom;
   $R^1$ and $R^2$ are taken together with the atom to which they are attached and represent a cyclobutyl ring, optionally substituted with 1-2 fluorine atoms, and $R^3$ represents hydrogen or a fluorine atom;
   or
   $R^1$ represents methyl,
   $R^2$ represents methyl or a fluorine atom and
   $R^3$ represents a fluorine atom.

2. The method of claim 1 wherein one of X and Y is O and the other is N, and Z is N.

3. The method of claim 1 wherein the compound is of structural formula II:

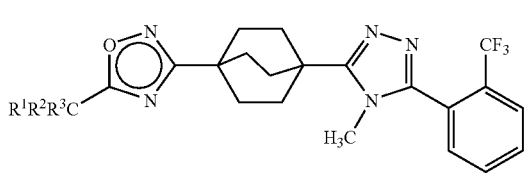

or a pharmaceutically acceptable salt thereof.

4. The method of claim 1 wherein the compound is selected from:
   5-(1,1-Difluoroethyl)-3-(4-{4-methyl-5-[2-(trifluoromethyl)phenyl]-4H-1,2,4-triazol-3-yl}bicyclo [2.2.2]oct-1-yl)-1,2,4-oxadiazole;

5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole 2-(1-Fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole or a pharmaceutically acceptable salt thereof.

5. The method of claim 1 wherein the compound is:
5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt thereof.

6. The method of claim 1 wherein the compound is:
5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt thereof.

7. The method of claim 1 wherein the compound is:
5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

or a pharmaceutically acceptable salt thereof.

8. The method of claim 1 wherein the compound is:
2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

or a pharmaceutically acceptable salt thereof.

9. The method of claim 1 wherein an additional anti-cancer agent is administered either simultaneously, separately or sequentially.

\* \* \* \* \*